US009006420B2

(12) United States Patent
Hillebrand

(10) Patent No.: US 9,006,420 B2
(45) Date of Patent: Apr. 14, 2015

(54) METHOD FOR CONCENTRATING AND ISOLATING BIOMOLECULES OR VIRUSES

(76) Inventor: Timo Hillebrand, Hoppegarten (DE)

( * ) Notice: Subject to any disclaimer, the term of this patent is extended or adjusted under 35 U.S.C. 154(b) by 393 days.

(21) Appl. No.: 12/941,783

(22) Filed: Nov. 8, 2010

(65) Prior Publication Data

US 2011/0117628 A1 May 19, 2011

Related U.S. Application Data

(63) Continuation of application No. PCT/EP2009/055596, filed on May 8, 2009.

(30) Foreign Application Priority Data

May 8, 2008 (DE) .......................... 10 2008 023 297

(51) Int. Cl.
*C12N 7/02* (2006.01)
*C07K 1/30* (2006.01)
*C07H 21/00* (2006.01)
*C12N 15/10* (2006.01)
*C07K 1/32* (2006.01)
*C12N 7/00* (2006.01)

(52) U.S. Cl.
CPC .............. *C12N 15/1003* (2013.01); *C07K 1/30* (2013.01); *C07K 1/32* (2013.01); *C12N 7/00* (2013.01); *C12N 2770/24351* (2013.01)

(58) Field of Classification Search
None
See application file for complete search history.

(56) References Cited

U.S. PATENT DOCUMENTS 5,739,019 A 4/1998 Walker et al.

FOREIGN PATENT DOCUMENTS

EP 1 739 094 A1 1/2007
WO WO 03/095079 A1 11/2003

OTHER PUBLICATIONS

Veith and Reynolds. Production of a High Gel Strength Whey Protein Concentrate from Cheese Whey. Journal of Dairy Science. 2004; 87(4): 831 840.*
Sharma, et al. One step purification of peanut phospholipase D by precipitation with alginate. Bioseparation. 2000; 9: 93-98.*
Braschler, et al. Gentle cell trapping and release on a microfluidic chip by in situ alginate hydrogel formation. Lab Chip. 2005; 5, 553-559.*
Moscoso, et al. Molecular Detection and Serotyping of Infectious Bronchitis Virus from FTA® Filter Paper. Avian Dis. 2005; 49:24-29.*
International Search Report issued Sep. 11, 2009 in PCT/EP2009/055596 (with Translation of Category of Cited Documents).
Sulakshana Jain, et al., "Applications of Alginate in Bioseparation of Proteins", Artificial Cells, Blood Substitutes, and Immobilization Biotechnology 2006, vol. 4, No. 2, XP009121281, 2006, pp. 127-144.
S. Teotia, et al., "One-step purification of glucoamylase by affinity precipitation with alginate", Journal of Molecular Recognition, vol. 14, No. 5, XP-002541150, Sep. 2001, pp. 295-299.
Frédéric De Ceuninck, et al., "Culture of chondrocytes in alginate beads", Methods in Molecular Medicine 2004, Database Medline [Online], Database Accession No. NLM15280584, XP-002541151, 2004, pp. 15-22 (Abstract only).

* cited by examiner

*Primary Examiner* — Louise Humphrey
(74) *Attorney, Agent, or Firm* — Oblon, McClelland, Maier & Neustadt, L.L.P.

(57) ABSTRACT

A simple and convenient method for concentrating a biomolecule, including protein or nucleic acid molecules, from a sample. Purified and isolated biomolecules obtained by this method. Methods for improving the specificity or sensitivity of detecting a biomolecule by concentration and/or purification or isolation of the biomolecule according to the method of the invention.

10 Claims, 3 Drawing Sheets

METHOD FOR CONCENTRATING AND ISOLATING BIOMOLECULES OR VIRUSES

CROSS-REFERENCE TO RELATED APPLICATIONS

This application is a continuation of PCT/EP2009/055596, filed May 8, 2009. Priority is also claimed to Germany 10 2008 023 297.1, filed May 8, 2008. Both of these prior applications are incorporated by reference in their entireties.

STATEMENT REGARDING FEDERALLY SPONSORED RESEARCH OR DEVELOPMENT (None)

REFERENCE TO MATERIAL ON COMPACT DISK (None)

BACKGROUND OF THE INVENTION

1. Field of the Invention

A simple and convenient method for concentrating a biomolecule, including protein or nucleic acid molecules, from a sample. Purified and isolated biomolecules obtained by this method. Methods for improving the specificity or sensitivity of detecting a biomolecule by concentration and/or purification or isolation of the biomolecule according to the method of the invention.

2. Description of the Related Art

The investigation of diagnostically relevant biological samples such as serum, plasma, blood, swab samples or organ triturations for detection of infectious pathogens has gained enormously in importance in recent years. Virus infections such as HIV, HCV or HBV are on the increase worldwide.

Commercially available methods for detecting viral nucleic acids are based on known nucleic acid amplification techniques such as PCR (polymerase chain reaction), real time PCR, NASBA (nucleic acid sequence-based amplification) or branched DNA detection. However, the known detection methods are pushing the limits of detection sensitivity, especially in the testing of large-volume samples (such as pools of 96 individual plasma samples). The problem lies in the fact that the commercial tests used always need isolation of the nucleic acids (for example, of viral type). Isolation of viral nucleic acids is usually performed from liquid samples with a volume of 50-200 µL.

In order to be able to achieve higher detection sensitivity or to be able to investigate even pooled individual samples more sensitively, methods for working up large-volume samples are needed. Since this is not possible with the common nucleic acid isolation methods, attempts have been made to concentrate virus particles of a sample in a first step. One possibility for concentrating viral particles consists in ultracentrifuging the sample to be investigated. In this way virus particles accumulate on the bottom of the test tube. This method depends on an ultracentrifuge, and is also time-consuming and unsuitable for routine diagnostics. Alternative methods consist in precipitation of virus particles by means of polyethylene glycol/sodium chloride, followed by centrifugation (Yamamoto et al., Virology 40 (1970) 734; Morandi et al., J. Clin. Microbiol. 36 (1998) 1543-1538). In these cases, various mixtures of PEG and sodium chloride are used and these reagents are mixed with the biological sample. Thereafter the mixture is incubated for a lengthy time in the cold and then the virus (protein)-NaCl/PEG precipitates are obtained by centrifugation. These methods are also laborious and need much time. Another problem is the further processing of the precipitates for isolation of the viral nucleic acids. In many cases the precipitates can be redissolved only with great difficulty. This greatly influences the efficiency and quality of nucleic acid isolation. DE Patent 19856415 C2 describes a method that includes the known NaCl/PEG precipitation, after which the nucleic acids are isolated in a manner known in itself by binding on a silicate solid phase. The extent to which this method is superior to the adequately known method of NaCl/PEG precipitation with the known problems is not clear. Furthermore, this method also needs incubation in the cold and twenty minutes of centrifugation.

The method supposedly makes it possible to isolate viral nucleic acids from a sample of up to 10 mL. A further commercially available variant, which supposedly permits processing up to 1-mL samples, is based on concentration of the viral nucleic acids using a special detergent. An initial incubation of the sample with a lysis reagent then leads to lysis of the viruses. Thereafter a "detergent-nucleic acid complex" is formed. The mixture is centrifuged and the pellet obtained is then treated by proteolysis, after which the nucleic acid is again isolated in a manner known in itself via binding on a silicate solid phase (QIAamp UltraSens Virus Handbook). In this case also; problems with resuspension of the pellet are mentioned. Furthermore, the method permits processing only of samples with a volume of at most 1 mL.

The content of unexamined disclosure WO 03/095079 A2 is a filter membrane based on completely polymerized alginate fibers as well as further support materials for concentrating and/or separating components from liquids. The components that are supposedly concentrated are protozoans. The technique is oriented toward the field of determination and concentration of microbiological components in drinking water, etc. What is described therein is a method for producing a special membrane layer (fleece) on the basis of a polyuronic acid polymer. A filter membrane is produced in a laborious process and then used for specific purposes. In the cited method, a liquid is passaged over a previously prepared filter membrane based on a polyuronic acid polymer. The cited disclosure does not give any information on how to dissolve the polymer in order to achieve subsequent isolation of nucleic acids from the biological sample or how to isolate a nucleic acid from viruses after they have been concentrated. Furthermore, there is no information on how viruses can be concentrated with the membrane, since the concentration principle is based on the fact that the protozoans are concentrated in well-defined pores formed in the polyuronic acid polymer. Isolation of nucleic acids from biological samples is neither described nor made obvious in WO 03/095079 A2. Furthermore, there is indication that the polymer is dissolved with a chaotropic buffer.

U.S. Pat. No. 5,739,019 A describes the isolation of microorganisms from an aqueous sample. The patent does not describe a method in which biomolecules are concentrated from a biological sample in polymers based on polyuronic acid, after which nucleic acids are isolated, but instead discloses a mechanism whereby polyuronic acid can be polymerized by addition of calcium chloride. The cited patent utilizes this mechanism, in which aqueous solution of potassium chloride and microorganisms is mixed dropwise with a polyuronic acid, and the microorganisms are then encapsulated in these droplets. These encapsulated microorganisms are then cultivated in so-called selective growth media in subsequent steps of the method. What is not done is subsequent isolation of nucleic acids from the biomolecules for diagnostic detection. No mention is made of the isolation of DNA.

The isolation of a virus is reported in Tribune de Cebedeau, 1976, 29 (390), pp. 186-94. Isolation of a nucleic acid is not mentioned. A membrane is produced in known manner by means of alginate and calcium chloride. A solution from which the viruses are supposedly adsorbed on the filter or in the filter is then passaged via this membrane filter (polymerized alginate filter system). Thus the method is used to concentrate viruses on or in membranes (or more correctly hydrogels) by filtering the liquid containing the viruses through this alginate membrane.

The described prior art methods clearly show that the processing of large-volume samples is still inherently complicated and associated with considerable disadvantages, as is also an increase of the volume of a sample in order to increase the sensitivity for detection of viral nucleic acids.

Heretofore it has not been described in the prior art that nucleic acids can be bound on or in polymerized alginate and then recovered. Heretofore it has also not been known that microorganisms (especially viruses) can be concentrated in order to isolate nucleic acids therefrom and in turn to detect the viruses after concentration.

BRIEF DESCRIPTION OF THE INVENTION

An object of the invention is therefore to enable the concentration of biomolecules or viruses in order to be able to process, in particular, large-volume samples. In this regard, the method is intended to be compatible with a subsequent simple and rapid technique for nucleic acid isolation. This object was achieved according to the features of the claims.

DETAILED DESCRIPTION OF THE PREFERRED EMBODIMENTS

Figure 3:
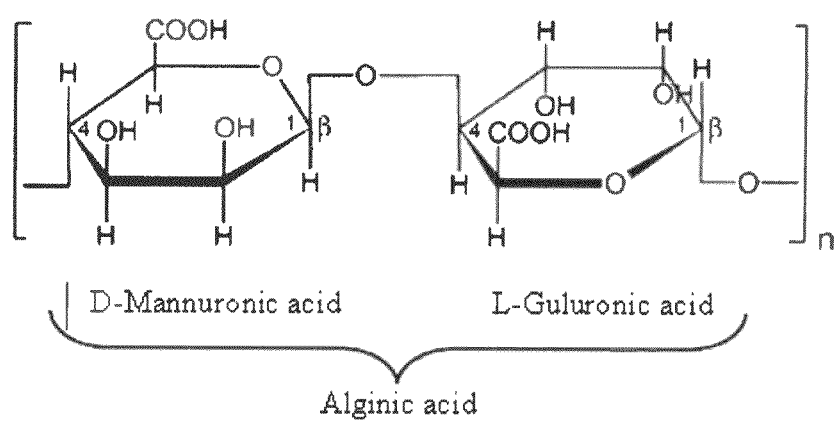
FIG. 3 depicts the chemical structure of an aliginic acid comprising D-mannuronic acid and L-guluronic acid.

Surprisingly it has been found that certain polysaccharide derivatives can be used very effectively for concentrating viruses in liquid samples, this concentration step being compatible with efficient methods for isolation of viral nucleic acids. The polysaccharide derivatives are the salts of polyuronic acids. In this regard the so-called alginates of the alginic acids are particularly suitable. Alginates are structure-forming elements of brown algae. Alginate is a polysaccharide composed of 1,4-linked α-L-guluronic acid (G) and β-D mannuronic acid (M), see FIG. 3:

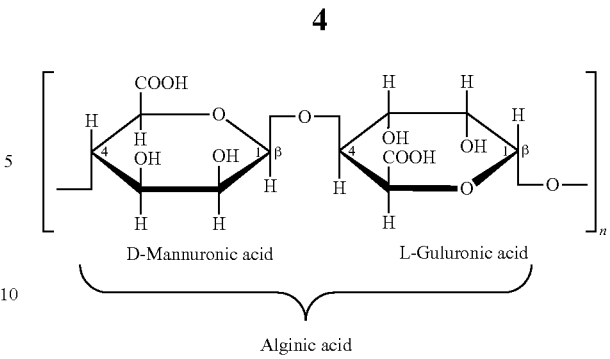

Alginic acid

Homopolymeric regions are formed in which mannuronic acid or guluronic acid is present as a block.

Alginates are used in the food, pharmaceuticals and cosmetics industries, for example as gelling agents in the food industry, as a finishing agent for textiles, for manufacture of photographic papers or in dental medicine for production of dental and jaw impressions.

Alginate is also an important biomaterial. By encapsulating human cell tissue with alginate, it is possible to store exogenous material such as donor cells in a manner protected from recognition and destruction by the immune system. However, there have been no suggestions of any kind that alginates can be used as materials for concentrating viruses for subsequent isolation and purification of nucleic acids.

For the inventive method, the known ability of alginates to undergo gelling and form so-called hydrogels in solutions with low calcium content is utilized. The cause of the gelling is based on the incorporation of calcium ions into the zig-zag structure of the GG blocks. The zig-zag structure of another alginate molecule is then deposited on this zone. As a result, three-dimensional structures are formed. The formation of gels also takes place in combination with strong acids. Furthermore, the gel structures obtained can also be destroyed again in specific manner.

By means of the inventive method, utilizing the formation of alginate gels, viruses in a liquid sample, especially in problematic large-volume samples, can be concentrated extremely simply and rapidly for subsequent molecular diagnostic analysis. This method is safe as regards use of chemicals and it does not need any kind of special equipment.

In one aspect the method for concentrating viruses from a sample for subsequent isolation of viral nucleic acids includes the following steps:
 (i) adding an aqueous alginate solution to a sample,
 (ii) adding an aqueous solution that induces gel formation/pellet formation (for example, use of a 1 M calcium chloride solution or of a 1% hydrochloric acid solution)
 (iii) mixing the sample and briefly incubating it at a suitable temperature, for example, at room temperature
 (iv) removing the supernatant, for example, by centrifuging the sample and removing the supernatant
 (v) dissolving the pellet or gel fragment and subsequently isolating viral nucleic acids in ways known in themselves In contrast to the prior art, what is used is not a completely polymerized membrane but instead two components that—brought into direct contact—can produce a gel, these components being brought into contact with a sample, from which the nucleic acids and/or other biomolecules are isolated. The gel fragment containing the concentrated biomolecules of the sample then becomes visible only after centrifugation. Before then, the sample is still liquid and not completely polymerized.

In contrast to the prior art, what is used is not a method in which cultivated microorganisms are present in an aqueous solution that already contains a complexing component (such as aqueous calcium chloride solution) after which quasi completely polymerized droplets, in which the microorganisms have then been incorporated, are obtained by dropwise addition of an alginate solution.

The inventive method differs from the method described in WO 03/095079 A2 bp the fact that it does not use a membrane based on polymerized polyuronic acid, but instead is based on the combination of a polyuronic acid with a biological sample and a subsequent component that permits gel formation. Consequently the biological sample is preserved and the polymer is formed only after completion of centrifugation, since not the entire sample becomes completely polymerized. In this way the inventive method is clearly distinguished from WO 03/095079 A2.

Another objective of the inventive method is to dissolve the polymer in order to achieve subsequent isolation of nucleic acids from the biological sample (and also to isolate a nucleic acid from viruses after these have been concentrated)

The concentrations of alginate and reagent used for gel formation in the inventive method are extremely low. From this it follows that the gelling process does not even take place visibly, as is known in the food industry or has been described for all applications of alginates.

After separation of the gel or pellet, e.g., after centrifugation, the supernatant is removed. A small gel fragment or pellet is visible at the bottom of the test tube, and this gel fragment/pellet contains the viruses concentrated from the sample. Thereafter the gel fragment/pellet is redissolved by adding a solution that destroys the gel structure. In the last step, the viral nucleic acids are then isolated from the concentrated sample by means of known methods for isolating nucleic acids. The method is extremely simple to perform. Incubation and subsequent centrifugation can be completed within 5 to 10 minutes. Dissolution of the gel fragment takes place without problems. The known problems with extremely difficult resuspendability of PEG/NaCl precipitates do not occur. Ultracentrifugation is not needed, and so normal standard bench centrifuges can be used. The volume of the liquid starting sample can be chosen as desired, thus permitting a very broad spectrum of use. For example, it is possible to work with samples of 500 µL or even 10 mL. Thus an enormously broad range of applications is achieved.

By virtue of the inventive method, the initial sample volume is reduced to the gel fragment/pellet produced in the inventive process, and it can then be further processed without problems in the so-called mini-format for nucleic acid isolation.

As an example of the inventive method, an aqueous alginate solution is combined with an aqueous solution containing salts of divalent or polyvalent cations (such as calcium chloride or aluminum chloride). Similarly, it is possible to combine an aqueous alginate solution and a weak acid (hydrochloric acid). Destruction of the gel structure can be achieved by means of a buffer solution containing a chelating agent (EDTA) or else by means of adding a solution of trisodium citrate dihydrate. It is also possible to dissolve the gel fragment/pellet in a low-salt buffer (such as 10 mM Tris HCl) at a basic pH.

A particularly efficient embodiment utilizes the observed effect that the resulting alginate gels can also be dissolved very effectively with buffers used for isolation of nucleic acids. Such so-called chaotropic buffers, for example on the basis of guanidinium salts, destroy alginate gels in a general manner, regardless of the method by which the alginate gel was formed. The specialized literature on alginates and their areas of application does not explain such an observed effect.

On the basis of this observation, the alginate gel can then be dissolved with a chaotropic buffer, which subsequently can be used simultaneously for the process of isolation of the viral nucleic acids in a dual function. In this preferred case, the alginate gel is dissolved with a chaotropic buffer after centrifugation and removal of the supernatant, and the mixture is then brought into contact with a mineral support material. Optionally, still other components (alcohols or detergents or mixtures of alcohols and detergents), which are capable of further improving the optimization of the binding of the viral nucleic acids to the mineral support material, can also be added to the chaotropic buffer. The bound nucleic acids are then washed and finally detached from the support material once again. As a rule, the isolation of viral nucleic acids via the inventive virus concentration from a large-volume sample can then be achieved within as little as approximately 30 minutes. The inventive method is therefore much simpler and faster than all other methods in this regard and also much faster than previously known techniques. Thus the inventive method solves the stated problem ideally.

A further diagnostic challenge relates to the isolation of so-called free or naked nucleic acids from biological samples. In this case also it would be desirable to use a large volume of the sample to be investigated (such as urine, serum, plasma), since the very low concentrations of free nucleic acids make it impossible to achieve a comprehensive diagnostic analysis by processing small sample volumes. A further increase in sensitivity can be achieved only by increasing the sample volume. However, no methods for doing so exist in laboratory practice.

Surprisingly, it has been found that, once again, salts of polyuronic acids, especially alginates or alginic acid, are also capable of concentrating nucleic acids from samples or can be used in general as material for isolation of nucleic acids in excellent manner. This is all the more unexpected because of the fact that not only nucleic acids but also alginates are known to be polyanions. In this respect it was already very surprising that even nucleic acids can be concentrated and subsequently isolated by means of these sugars. For this reason the inventive method again makes use of the sequence that has also been described for the concentration of viruses from samples:

(i) adding an aqueous alginate solution to the sample
(ii) adding an aqueous solution that induces gel formation (for example, use of a 1 M calcium chloride solution or of a 1% hydrochloric acid solution)
(iii) mixing the sample and briefly incubating it at room temperature
(iv) centrifuging the sample and removing the supernatant
(v) dissolving the gel fragment Isolation of the concentrated free nucleic acids can again be achieved by dissolving the gel fragment/pellet with already described buffers and then isolating the nucleic acids with methods known in themselves, for example by binding on mineral solid phases. It is again also possible to use chaotropic buffers to dissolve the gel fragment/pellet and subsequently to perform isolation of the nucleic acids. However, purification can also be achieved with traditional methods, for example precipitation of the nucleic acids.

A particularly simple method for isolating free nucleic acids from samples consists in mixing the sample with an aqueous alginate solution and an acid. After centrifugation, the supernatant is removed and the gel fragment is dissolved with a basic low-salt buffer (such as 10 mM Tris-HCl; pH 9). Purification of the nucleic acids is not necessary. The solution can be used immediately, for example for PCR applications. In this way it is shown that the alginates can also boost the amplification reaction.

Such a purification variant is completed in a few minutes and represents the very simplest isolation of nucleic acids. In summary, once again it comprises the following steps:
(i) adding an aqueous alginate solution to the sample
(ii) adding an acid to the sample
(iii) mixing the sample and briefly incubating it at room temperature
(iv) centrifuging the sample and removing the supernatant
(v) dissolving the gel fragment in a low-salt buffer having slightly alkaline pH
(vi) using the isolated nucleic acid immediately in a PCR Even for this special embodiment, there is practically no limitation with respect to the volume of the sample.

The inventive method is also suitable in general for isolating nucleic acids, such as RNA or DNA, from a sample. If the nucleic acids to be isolated are not present as free nucleic acids, the sample can be lysed in a form known in itself. The nucleic acids liberated in this way from the sample are then isolated once again in accordance with the inventive method. In this case also it is possible, after dissolution of the gel fragment (which contains the concentrated nucleic acid), to perform "traditional" purification of the nucleic acids or to use the solution obtained after dissolution of the gel fragment by means of the described basic low-salt buffer directly for a PCR reaction.

Besides the described concentration of viruses from the most diverse samples, the concentration of "naked nucleic acids" and also the concentration of nucleic acids that are not "free", other biomolecules, such as proteins, enzymes, antibodies or cell receptors of a sample are also concentrated unspecifically by means of the described methods. Just as the nucleic acids, these substances can then be used in ways known to the person skilled in the art for further downstream applications.

In this way the inventive method represents a novel and universal option for concentrating the most diverse biomolecules for specific processing. It can be performed extremely rapidly and simply and also does not need any kind of special instruments.

The universal nature of the invention will be explained in more detail hereinafter on the basis of exemplary embodiments, but the Examples of exemplary embodiments below do not represent any limitations of the inventive method.

EXAMPLES

Exemplary Embodiment 1

Concentration of Nucleic Acids in a Lysed Biological Sample and Subsequent Direct Use of the Reliberated Nucleic Acids for a PCR The nucleic acids were concentrated and subsequently isolated from a swab sample (smear of oral mucous membrane), using the following procedure:
(i) Insert swab into a 1.5 mL test tube. Add 400 µL lysis buffer (5% Triton X-100, 0.1 M guanidine hydrochloride) and 10 µL proteinase K (20 mg/mL). Incubate at 50° C. for 5 minutes. Squeeze out swab and discard.
(ii) Add 10 µL of an aqueous alginate solution (1%) and 50 µL 1% hydrochloric acid. Vortex and incubate at RT for 2 minutes.
(iii) Centrifuge at maximum speed for 1 minute. Remove supernatant completely.
(iv) Add 1 mL water and centrifuge at maximum speed for 1 minute. Remove supernatant completely.
(v) Add 200 µL of a low-salt buffer (10 mM Tris HCl; pH 9). Resuspend gel fragment/pellet and then dissolve completely.

The isolated DNA was subsequently used for a PCR for amplification of a human-specific nucleic acid sequence. The result shows the suitability of the nucleic acid for PCR application.

Figure 1:
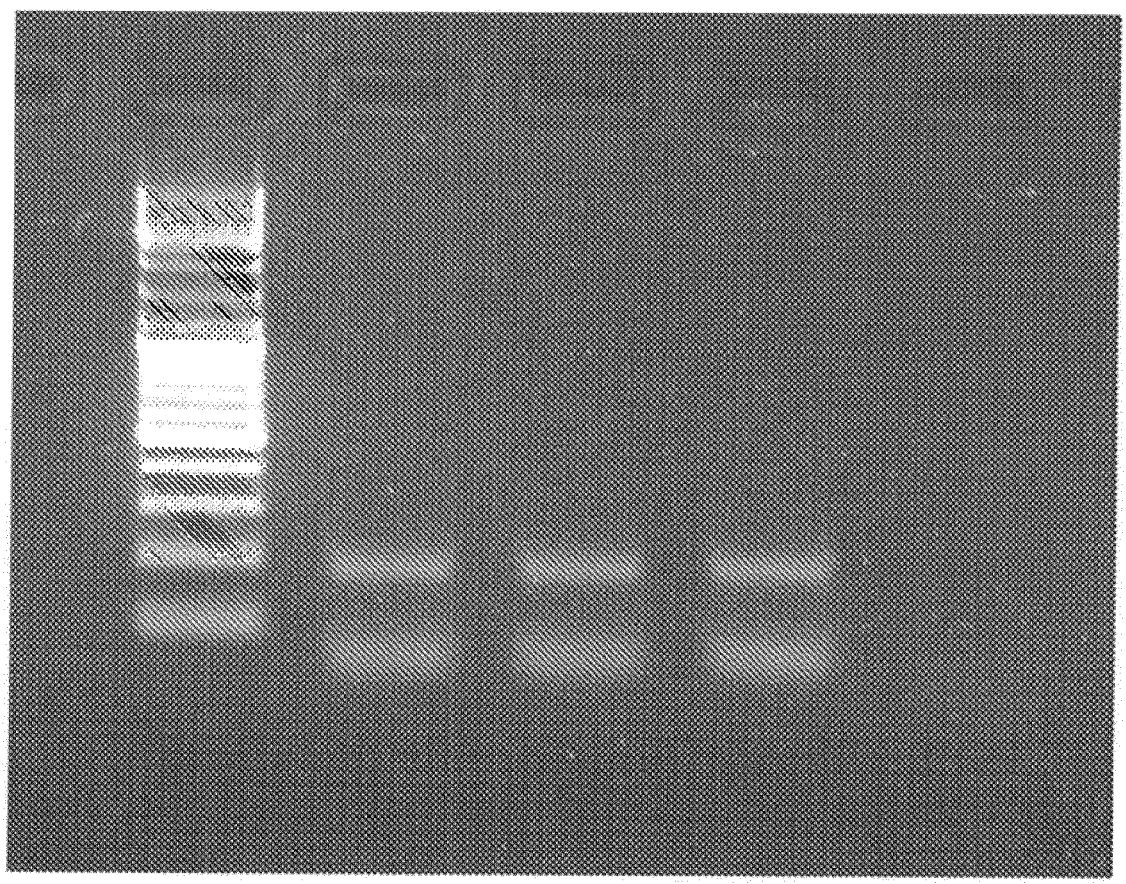
FIG. 1 shows the detection of the amplification product on an agarose gel. The reference numerals in FIG. 1 denote:
 1—DNA length standard
 2—4 amplification products
 5—PCR blank value

FIG. 1 shows the detection of the amplification product on an agarose gel. The reference numerals in FIG. 1 denote: 1—DNA length standard; 2—4 amplification products AND; 5—PCR blank value.

Exemplary Embodiment 2

Concentration of Free Nucleic Acids ("Naked" Nucleic Acids) from a Large-Volume Sample in Combination with Subsequent Nucleic Acid Purification A DNA fragment of 560 bp was spiked in 5 mL of an aqueous sample (triple determination). The sample was transferred into a 15 mL centrifuge tube. The free nucleic acids were isolated as follows:
(i) Add 100 µL of an aqueous alginate solution (1%) and 500 µL 1% hydrochloric acid. Vortex and incubate at RT for 5 minutes.
(ii) Centrifuge at 4500 rpm for 10 minutes. Remove supernatant completely.
(iii) Resuspend the gel fragment with 500 µL of a chaotropic salt solution (4 M guanidine isothiocyanate).
(iv) Transfer the mixture onto a spin filter column containing glass-fiber material (Whatmann GFD). Centrifuge at 12,000 rpm for 1 minute. Discard the filtrate.
(v) Wash the spin filter column with an ethanol-containing washing buffer (80% ethanol). Centrifuge at 12,000 rpm for 1 minute. Discard the filtrate.
(vi) Dry the spin filter column by centrifuging briefly.
(vii) Insert the spin filter column in a new test tube. Add 100 µL of a low-salt buffer (10 mM Tris HCl) and elute the nucleic acid from the column.

The isolated free nucleic acid was subsequently applied onto an agarose gel. As can be seen, almost quantitative recovery was achieved with the method.

Figure 2:
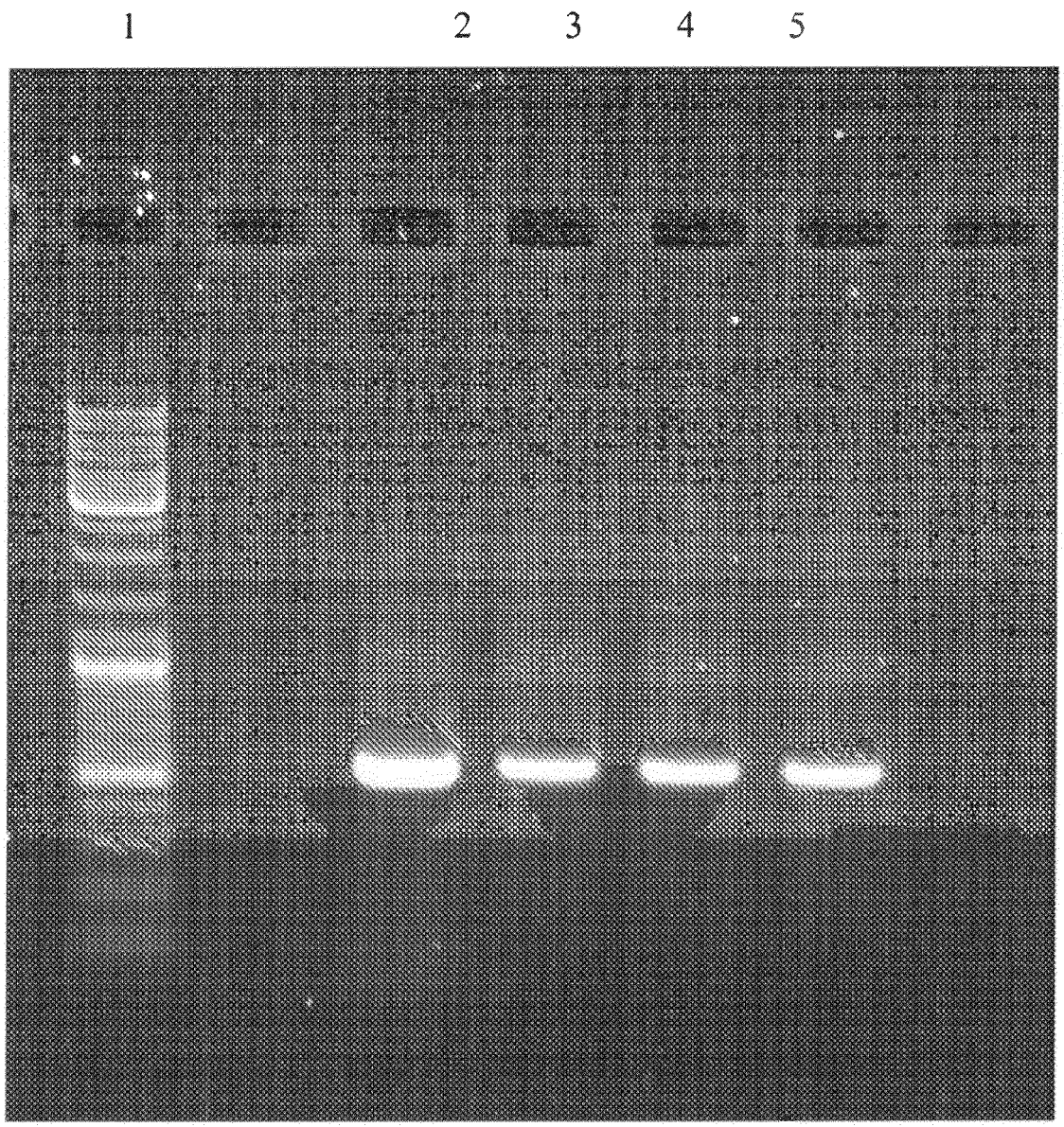
FIG. 2 shows the gel-electrophoresis diagram of the recovered DNA fragment. The reference numerals in FIG. 1 denote:
 1—DNA length standard
 2—DNA fragment before purification
 3—5 DNA fragments after purification from 5 mL water

FIG. 2 shows the gel-electrophoresis diagram of the recovered DNA fragment. The reference numerals in FIG. 2 denote: 1—DNA length standard; 2—DNA fragment before purification; and 3—5 DNA fragments after purification from 5 mL water.

Exemplary Embodiment 3

Viral Concentration and Subsequent Isolation of the Viral Nucleic Acids. Proof of the Distinct Increase of Sensitivity by Use of a Larger Sample Volume Serum containing BVD viruses was added in various concentrations to a cell culture medium. 1.8 mL of the sample was used for concentration of the viruses. Compared with the concentration technique, the viral nucleic acid was isolated from 200 µL of the sample by means of a standard method. Detection of the BVD viruses was achieved with a commercial real-time test system. Two samples of each dilution were analyzed. The CT values listed in the table are the average values from the two samples. The viruses were concentrated as follows:

(i) Transfer 1.8 mL of the virus-containing cell culture sample into a 2.0 mL test tube. Add 25 μL of an aqueous alginate solution (1%) and 200 μL 1% hydrochloric acid to the cell culture medium (2 mL). Vortex and incubate at RT for 10 minutes.

(ii) Centrifuge at 14,000 rpm for 2 minutes. Remove supernatant completely.

(iii) Resuspend the gel fragment with 500 μL of a chaotropic salt solution (4 M guanidine isothiocyanate).

The viral nucleic acids were subsequently isolated on an automatic extraction system (InnuPURE® C12; Analytik Jena AG). For this purpose a commercial kit (innuPREP Virus RNA Kit; Analytik Jena AG) was used.

Using the commercial kit, 200 μL, samples were also worked up directly on an automatic extraction system (InnuPURE® C12; innuPREP RNA Kit C12; Analytik Jena AG).

Thereafter the isolated nucleic acid was used for detection of the virus by means of real-time PCR.

The results of the real-time PCR are presented below.

Results of the real-time PCR—Comparison of the "standard method" with the inventive concentration method

|  | "Direct method" using 200 μL sample | Concentration method using 1.8 mL sample |
| --- | --- | --- |
| Dilution 1 | CT 32.8 | CT 31.4 |
| Dilution 2 | CT 36.2 | CT 33.5 |
| Dilution 3 | CT 39.7 | CT 37.7 |

Thus it is clear that a larger sample volume can be processed with the inventive concentration method. This results in the advantage of higher sensitivity, especially when the number of viruses to be detected is small. In this way it is shown that the inventive method offers an option for processing larger sample volumes and therefore achieving higher detection sensitivity.

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinency of the cited documents is reserved.

The invention claimed is:

1. A method for concentrating or isolating a nucleic acid comprising:
    a) contacting a sample containing the nucleic acid with an aqueous solution of at least one salt of a polyuronic acid to form a mixture;
    b) adding at least one substance that induces gel formation of the at least one salt of the polyuronic acid in the mixture;
    c) isolating the gel formed in (b) from liquid components of the mixture; and
    d) recovering the nucleic acid from the isolated gel, thereby concentrating or isolating the nucleic acid.

2. The method of claim 1, wherein the salt of the polyuronic acid is alginate.

3. The method of claim 1, wherein said at least one substance that induces gel formation of the salt of the polyuronic acid is at least one acid, at least one solution containing calcium ions, or a combination thereof.

4. The method of claim 1, comprising adding in (b) at least one calcium solution at a concentration of calcium ions of 1 mol/L.

5. The method of claim 1, comprising adding in (b) at least one acid at a concentration of 1% w/v.

6. The method of claim 1, wherein isolating the gel in (c) comprises centrifuging the sample and removing the supernatant.

7. The method of claim 1, wherein the nucleic acid is recovered in (d) by dissolving the gel and isolating the nucleic acid from the dissolved gel.

8. The method of claim 1, wherein the nucleic acid is recovered by dissolving the gel with at least one agent selected from the group consisting of an alkali, a chelating agent, and a chaotropic salt.

9. The method of claim 1, wherein the nucleic acid is recovered by dissolving the gel with at least one compound selected from the group consisting of EDTA, a guanidinium salt, or a citrate.

10. The method of claim 1, wherein the sample contains a virus and the virus is subjected to lysis prior to (a) or after (d).

* * * * *